United States Patent
Miller et al.

(10) Patent No.: US 7,652,167 B2
(45) Date of Patent: Jan. 26, 2010

(54) PROCESS FOR PRODUCTION OF ORGANIC ACID ESTERS

(75) Inventors: Dennis J. Miller, Okemos, MI (US); Navinchandra Asthana, East Lansing, MI (US); Aspi Kolah, East Lansing, MI (US); Carl T. Lira, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 482 days.

(21) Appl. No.: 10/894,307

(22) Filed: Jul. 19, 2004

(65) Prior Publication Data
US 2006/0014977 A1 Jan. 19, 2006

(51) Int. Cl.
*C07C 69/66* (2006.01)
(52) U.S. Cl. .................................................... 560/179
(58) Field of Classification Search ................. 560/179
See application file for complete search history.

(56) References Cited

U.S. PATENT DOCUMENTS

| | | | |
|---|---|---|---|
| 1,400,849 A | 12/1921 | Backhaus | |
| 2,334,524 A * | 11/1943 | Wenker | 562/589 |
| 2,405,646 A * | 8/1946 | Filachione et al. | 560/179 |
| 2,610,206 A | 9/1952 | Campbell et al. | |
| 4,370,491 A | 1/1983 | Bott et al. | |
| 4,435,595 A | 3/1984 | Agreda et al. | |
| 5,008,046 A | 4/1991 | Bremus et al. | |
| 5,405,992 A | 4/1995 | Funk et al. | |
| 5,470,542 A | 11/1995 | Stringaro | |
| 5,536,856 A | 7/1996 | Harrison et al. | |
| 5,723,639 A | 3/1998 | Datta et al. | |
| 5,750,732 A | 5/1998 | Verser et al. | |
| 6,291,703 B1 | 9/2001 | Schaerfl et al. | |
| 6,342,626 B1 * | 1/2002 | Kaimal et al. | 560/179 |
| 2002/0144600 A1 | 10/2002 | TeGrotenhuis et al. | |
| 2005/0096481 A1 * | 5/2005 | Hildebrandt et al. | 560/55 |

FOREIGN PATENT DOCUMENTS

| | | |
|---|---|---|
| EP | 1 300 387 | 4/2003 |
| GB | 1294371 | 10/1972 |
| WO | WO2005/051885 | 6/2005 |

OTHER PUBLICATIONS

Omota, F., et al., Chem. Eng. Sci. 58 3159-3174 (2003).

(Continued)

*Primary Examiner*—Taylor Victor Oh
(74) *Attorney, Agent, or Firm*—Ian C. McLeod

(57) ABSTRACT

A process for producing organic acid esters using continuous countercurrent reactive distillation using acid catalysts in a structured packing in a single column (10) is described. In the reactive distillation an organic acid ester is formed by chemical reaction and can be purified to its final state within the single column. Organic acid esters are produced at relatively low cost, with less waste production, and in a less complicated manner than prior processes. Organic acid ester have uses as solvents, as intermediate chemicals, and in consumer products.

19 Claims, 6 Drawing Sheets

(Example 5)

La: Lactic acid; EtOH: Ethanol; EtLa: Ethyl lactate

OTHER PUBLICATIONS

Watkins, K., Chemical & Engineering News 80(2), 15 (2002).
Omota, F., et al., Chem. Eng. Sci. 58 3175-3185 (2003).
Smejkal, Q., et al., Chem. Eng. Sci. 56 365-370 (2001).
Asthana, Navinchandra et al., "Reactive distillation for the biorefinery: Production of organic acid esters" Preprints of Symposia—American Chemical Society, Division of Fuel Chemistry, 50(2), 683-684 Coden: PSADFZ; ISSN: 1521-4648, 2005, XP008089894.
Choi, Jong II et al., "Reaction kinetics of lactic acid with methanol catalyzed by acid resins", InternationalJournal of Chemical Kinetics, 28(1), 37-41 Coden IJCKBO; ISSN: 0538-8066, 1996, XP001057571.
McKetta et al. (Encyclopedia of Chemical Processing and Design, Chapter 19, 381-402), 1978.
Kirk and Othmer "Elastomers Polyisoprene to Expert Systems". Encyclopedia of Chemical Technology, 4th Edition, John Wiley & Sons, New York 9 755-780 (1997).
Seo, et al., Korean Journal of Chemical Engineering 16(5), 556-561 (1999).
Choi, J.I., et al., Journal of chemical Engineering of Japan 32(2), 184-189 (1999).
Benedict, D.J., et al., Ind. Eng. Chem. Res. 42 (2003).
Feng, X., et al., Chem. Eng. Sci. 51(20), 4673-4679 (1996).
Jafar, J.J., et al., J. Membrane Science 199, 117-123 (2002).
Walsh, K., Chemical Week 161(40), 23 (1999).
Steinigeweg, S., et al., Ind. Eng. Chem. Res. 41:5483-5490 (2002).
Popken, T., et al., Ind. Eng. Chem. Res. 40:1566-1574 (2001).
Hanika, J., et al., Chem. Eng. Sci. 54:5205-5209(1999).

* cited by examiner

Fig. 1 (Example 5)

*La: Lactic acid; EtOH: Ethanol; EtLa: Ethyl lactate*

Fig: 2 (Example 10)

*La: Lactic acid; MeOH: Methanol; MeLa: Methyl lactate*

Fig: 3 (Example 12)

PROCESS FOR PRODUCTION OF ORGANIC ACID ESTERS

CROSS-REFERENCE TO RELATED APPLICATIONS

None

STATEMENT REGARDING FEDERALLY SPONSORED RESEARCH OR DEVELOPMENT

None

BACKGROUND OF THE INVENTION (1) Field of the Invention

The present invention relates generally to a process for the countercurrent, reactive distillation, esterification of organic acids or esters with lower alcohols (C1 to C8). Specifically, the present invention relates to lactic acid esterification using reactive distillation with the alcohols, particularly ethanol. The present invention also preferably provides for recycling of dimers and trimers and other short-chain oligomers of lactic acid to improve yields.

(2) Description of the Related Art

Reactive distillation was first described in U.S. Pat. No. 1,400,849 to Backhaus. Backhaus discloses a continuous process of manufacturing organic acid esters comprising passing an organic acid in countercurrent fashion to a gradually increasing concentration of an alcohol. Backhaus specifically teaches a process of manufacturing methyl acetate using reactive distillation where methyl acetate and methanol are collected from the top of the reactive distillation column. The methyl acetate and methanol are then separated by a device such as a dephlegmator and/or a second column. The catalyst is an acid which is consumed in the reaction. Other prior approaches to producing organic acid esters (McKetta, John J., et al., Energy, Costing Thermal Electric Power Plants to Ethanol, Encyclopedia of Chemical Processing and Design, Marcell Dekker, Inc.), Vol. 19 381-402 (1976); Kirk and Othmer, "Elastomers, Polyisoprene to Expert Systems". Encyclopedia of Chemical Technology, 4$^{th}$ Edition, John Wiley & Sons, New York 9 755-780 (1997)) involve batch processes, which are labor intensive, can create waste, such as with the use of a mineral acid catalyst which is consumed, and require an excess quantity of alcohol (Kaimal, T. N. B., et al., U.S. Pat. No. 6,342,626).

Conventional continuous processes for making organic acid esters typically require a large amount of equipment and high energy costs. McKetta et al. (Encyclopedia of Chemical Processing and Design, Chapter 19, 381-402) disclose batch and continuous processes for the production of either volatile or non-volatile esters using acid resin catalysts. Kirk-Othmer (ibid) discloses batch and continuous processes for the production of esters using resin catalysts. Kirk-Othmer and McKetta et al. do not disclose a continuous process of producing lactic acid esters within a single reactive distillation column. U.S. Pat. No. 6,342,626 to Kaimal et al. discloses a catalyst-free process for the conversion of lactic acid to an alkyl ester which comprises simultaneous hydrolysis of dimers or higher polymers of lactic acid to free lactic acid and the esterification of the free lactic acid at a temperature in the range of 130° C. to 250° C. for four to eleven hours at a pressure of 5 to 25 kg/cm$^2$.

Organic acid esters can also be made directly from polymer precursors; in particular, ethyl lactate can be made by reacting ethanol with the precursor dilactide. The dilactide is quite expensive, however, as it requires several reaction steps to produce and purify.

Batch reactive distillation has been used (Seo, Y., W., et al., Korean Journal of Chemical Engineering 16(5), 556-561 (1999); and Choi, J. I., et al., Journal of Chemical Engineering of Japan 32(2), 184-189 (1999)) for making esters. Seo et al. (Korean J. Chem. Eng. 16(5), 556-561 (1999)) disclose a batch lactic acid esterification process using a strongly acidic cation exchange resin as a step for the recovery of high purity lactic acid. A low concentration of lactic acid solution of 20 weight percent or less is used, since it was believed that overall lactic acid yield decreases with higher feed concentrations of lactic acid. The esterification reaction was carried out in a reboiler and the methyl lactate, water and unreacted methanol were distilled upward through the distillation column. Methanol was recycled to the reboiler, while water and methyl lactate were recovered from the bottom of the reboiler. Seo et al. disclose a weight fraction of methyl lactate in the bottom product of the esterification column of approximately thirty percent or less. This reference discloses only batch distillation.

Choi et al. (J. Chem. Eng. Of Japan 32(2), 184-189 (1999)) disclose a batch lactic acid esterification process using a strongly acidic cation exchange resin as a step for the recovery of high purity lactic acid. A low concentration of lactic acid solution of 20 weight percent or less was used, since overall lactic acid yield decreased with higher feed concentrations of lactic acid. The esterification reaction was carried out in a feed vessel and the methyl lactate, water and unreacted methanol were distilled upward through the distillation column. Methanol was recycled to the feed vessel, while water and methyl lactate were removed to a reboiler where hydrolysis occurs after being condensed.

A more recent approach is the use of membranes (Benedict, D. J., et al., Ind. Eng. Chem. Res. 42 (2003); Feng, X., et al., Chem. Eng. Sci. 51(20), 4673-4679 (1996); Jafar, J. J., et al., J. Membrane Science 199, 117-123 (2002); Walsh, K., Chemical Week 161(40), 23 (1999); and Datta, R., et al., U.S. Pat. No. 5,723,639 (1998)); for example, there is a process that has been developed at Argonne National Laboratory in which water produced in esterification is removed through a membrane. However, membranes are susceptible to fouling. U.S. Pat. No. 5,723,639 to Datta et al., for example, discloses a process of esterification of fermentation derived organic acids such as lactic acid using pervaporation. The methods described by Datta et al., Benedict et al., Feng et al., and Jafar et al. each require a pervaporation membrane.

Other alternative methods of purification of esterification products have been described. U.S. Pat. No. 5,405,992 to Funk et al. discloses a process of continuous esterification with concurrent separation of the products upon a solid bed used as both an esterification catalyst and as an adsorbent for at least one of the esterification products.

The applications of reactive distillation have been focused on esters of acetic acid (Steinigeweg, S., et al., Ind. Eng. Chem. Res. 41:5483-5490 (2002); Popken, T., et al., Ind. Eng. Chem. Res. 40:1566-1574 (2001); Hanika, J., et al., Chem. Eng. Sci. 54:5205-5209 (1999); and Agreda, V. H., et al., U.S. Pat. No. 4,435,595 (1984)). Steinigeweg et al. disclose a reactive distillation process for the production of n-butyl acetate. Steinigeweg et al. vary several operational conditions and two different feed position setups were studied. Popken et al. disclose a one-feed and a two-feed reactive distillation process for the production of methyl acetate. Popken et al. breaks the binary azeotrope of methyl acetate-water by the extraction of the water by acetic acid feed. A pure, dry acetic acid feed is required to achieve a high purity methyl acetate in the distillate. Hanika et al. disclose a catalytic distillation process for the production of butylacetate. U.S. Pat. No. 4,435,595 to Agreda et al. discloses a reactive distillation process for producing high purity methyl acetate which achieves high reactant conversion. Neither Steinigeweg et al., Popken et al. Hanika et al. or Agreda et al. disclose a continuous process of producing high purity lactic acid or acid esters other than acetic acid ester within a single reaction column.

There has also recently been a study reported for the formation of fatty acid esters using reactive distillation (Omota, F., et al., Chem. Eng. Sci. 58 3159-3174 (2003); and Omota, F., et al., Chem. Eng. Sci. 58 3175-3185 (2003)). Omota et al. (Parts 1 and 2) describe fatty acid esterification by reactive distillation in the presence of a metal catalyst and in the absence of water. Smejkal, Q., et al., Chem. Eng. Science 56 365-370 (2001) describe the preparation of methyl propyl acetate from acetic acid and 2-methyl propanol. No aqueous feed solutions were used.

U.S. Pat. No. 5,008,046 to Bremus et al. describes a reactive distillation process using a column with plate type column with an acid catalyst under pressure. U.S. Pat. No. 5,536,856 to Harrison et al. describes a similar column wherein resin acid catalyst particles were supported by a tray on the column. The use of columns with trays is quite expensive.

Transesterification has been carried out in distillation columns. U.S. Pat. No. 4,370,491 to Bott et al. discloses a process for the preparation of acetic acid esters by alkali-catalyzed trans-esterification of an acetic acid ester with an alcohol carried out in the middle section of a distillation column wherein the alkaline catalyst is introduced into the upper part of the column, an alcohol is fed into the upper zone, and an ester is fed into the lower zone. Bott et al. does not disclose a continuous process of lactic acid ester trans-esterification within a single reaction column.

While the related art teaches organic acid esterification processes, there still exists a need for improved continuous processes for lower acid (C3 to C8) esterification and trans-esterification of the resulting esters.

OBJECTS

Therefore, it is an object of the present invention to provide an improved process for the continuous production of organic acid esters in a single column using reactive distillation. It is further a preferred object of the present invention to provide for recycling of dimers, trimers and higher oligomers which may be generated in the process, particularly in the production of lactate esters. Lactoyl lactate is the linear dimer hereafter referred to as "dimer" and Lactoyl lactoyl lactate is the linear trimer hereafter referred to as "trimer".

It is further an object of the present invention to provide a process for the continuous transesterification of organic acid esters in a single column using reactive distillation.

These and other objects will become increasingly apparent by reference to the following description.

SUMMARY OF THE INVENTION

The present invention relates to a process for the continuous esterification of an organic acid to produce an organic acid ester in a single vertical column by reactive distillation comprising:
(a) feeding a mixture of an organic acid containing about 10 to 80% water by weight and containing between 2 to 8 carbon atoms into an upper port of the column and an alcohol containing 1 to 8 carbon atoms into a lower port of the column;
(b) contacting in a reactive distillation column, the organic acid and the alcohol in countercurrent flow in a reaction zone between the ports at a temperature which reacts the organic acid and the alcohol over an insoluble acid catalyst mounted in structured packing elements and supported as a single unit of the elements in the column within the reaction zone to form the organic acid ester;
(c) removing vaporized unreacted alcohol and water from the top of the column, preferably the alcohol is recycled into the lower port of the column; and
(d) collecting a product comprising the organic acid ester from the bottom of the column, wherein the organic acid ester is partially reboiled by a heat exchanger at the bottom of the column so as to heat the organic acid and the alcohol in the reaction zone. The esters are other than acetic acid esters or other low boiling acetic acid esters.

The present invention further relates to a process for the continuous esterification of lactic acid to produce a lactic acid ester in a single vertical column by reactive distillation comprising:
(a) feeding a mixture of lactic acid Containing about 10 to 80% water by weight into an upper port of the column and an alcohol containing 1 to 8 carbon atoms into a lower port of the column;
(b) contacting in a reactive distillation column, the lactic acid and the alcohol in countercurrent flow in a reaction zone between the ports at a temperature which reacts the lactic acid and the alcohol over an insoluble acid catalyst mounted in structured packing elements and supported in the column within the reaction zone to form the lactic acid ester;
(c) removing vaporized unreacted alcohol and water from the top of the column; and preferably the alcohol is recycled into the lower port of the column; and
(d) collecting a product comprising the lactic acid ester from the bottom of the column, wherein the lactic acid ester is partially reboiled by a heat exchanger at the bottom of the column so as to heat the lactic acid and the alcohol in the reaction zone. Preferably the insoluble acid catalyst is an acidic ion exchange resin. Preferably the feeding of the alcohol relative to the lactic acid is such that a molar ratio of alcohol to lactic acid is maintained between about 1.5 to about 10.0. Preferably the feeding of the alcohol relative to the feeding of the lactic acid is such that the lactic acid conversion is greater than 50 percent.

The present invention also relates to a process for the continuous transesterification of an organic acid ester in a single column by reactive distillation comprising:
(a) feeding a first organic acid ester of a first alcohol containing 1 to 8 carbon atoms into a top port of the column, and a second alcohol containing 2 to 8 carbon atoms into a bottom port of the column;
(b) contacting in a reactive distillation column, the first lactic acid ester of the first alcohol and the second alcohol with an acid catalyst supported in the column to form a second lactic acid ester and the first alcohol;
(c) removing the first alcohol and remaining of the second alcohol from the top of the column; and
(d) collecting a product comprising the second organic acid ester of the second alcohol from the bottom of the column. Preferably the catalyst is an acidic ion exchange resin mounted in structured packing elements. Preferably the organic acid is lactic acid. Preferably the first lactic acid ester of a first alcohol is methyl lactate and the second alcohol is ethanol. Preferably the feeding rate of the ethanol relative to the feeding rate of the methyl lactate is such that a mole composition of the product is greater than fifty percent (50%) ethyl lactate. Preferably the feeding rate of the ethanol relative to the feeding rate of the methyl lactate is such that the percentage of methyl lactate conversion to ethyl lactate is greater than fifty percent (50%). Preferably the first lactic acid ester is subsequently produced in the same or similar type of column as the second lactic acid ester.

The present invention also relates to a process for the continuous esterification of a hydroxylated organic acid to produce an organic acid ester in a vertical column by reactive distillation comprising:
(a) feeding a mixture of an organic acid containing about 10 to 80% water by weight and containing between 2 to 8 carbon atoms into an upper port of the column and an alcohol containing 1 to 8 carbon atoms into a lower port of the column;

(b) contacting in a reactive distillation column, the organic acid and the alcohol in countercurrent flow in a reaction zone between the ports at a temperature which reacts the organic acid and the alcohol over an insoluble acid catalyst mounted in structured packing elements and supported as a single unit of the elements in the column within the reaction zone to form the organic acid ester;

(c) removing vaporized unreacted alcohol and water from the top of the column;

(d) collecting a product comprising the organic acid ester and dimers, trimers and higher oligomers and esters of the dimers, trimers, and higher oligomers of the hydroxylated acid from the bottom of the column;

(e) separating the organic acid ester from the dimers, trimers, and higher oligomers and their esters;

(f) hydrolyzing the dimers and trimers and higher oligomers and their esters to the organic acid in a second column; and (g) recycling the organic acid of step (f) with the organic acid fed into the column, wherein the organic acid ester is reboiled by a heat exchanger at the bottom of the column so as to heat the organic acid and the alcohol in the reaction zone.

The present invention also relates to a process for the continuous esterification of lactic acid to produce a lactic acid ester in a vertical column by reactive distillation comprising:

(a) feeding a mixture of lactic acid containing about 10 to 80% water by weight into an upper port of the column and an alcohol containing 1 to 8 carbon atoms into a lower port of the column;

(b) contacting in a reactive distillation column, the lactic acid and the alcohol in countercurrent flow in a reaction zone between the ports at a temperature which reacts the lactic acid and the alcohol over an insoluble acid catalyst mounted in structured packing elements and supported in the column within the reaction zone to form the lactic acid ester;

(c) removing vaporized unreacted alcohol and water from the top of the column;

(d) collecting a product comprising the lactic acid ester and dimers, trimers, and higher oligomers and esters of the dimers, trimers, and higher oligomers of the lactic acid from the bottom of the column;

(e) separating the lactic acid ester from the dimers, trimers and higher oligomers and their esters;

(f) hydrolyzing the dimers and trimers and higher oligomers and their esters to the lactic acid in a second column; and (g) recycling the lactic acid of step (f) with the lactic acid fed into the column, wherein the lactic acid ester is reboiled by a heat exchanger at the bottom of the column so as to heat the lactic acid and the alcohol in the reaction zone.

DETAILED DESCRIPTION OF THE INVENTION

Figure 1:
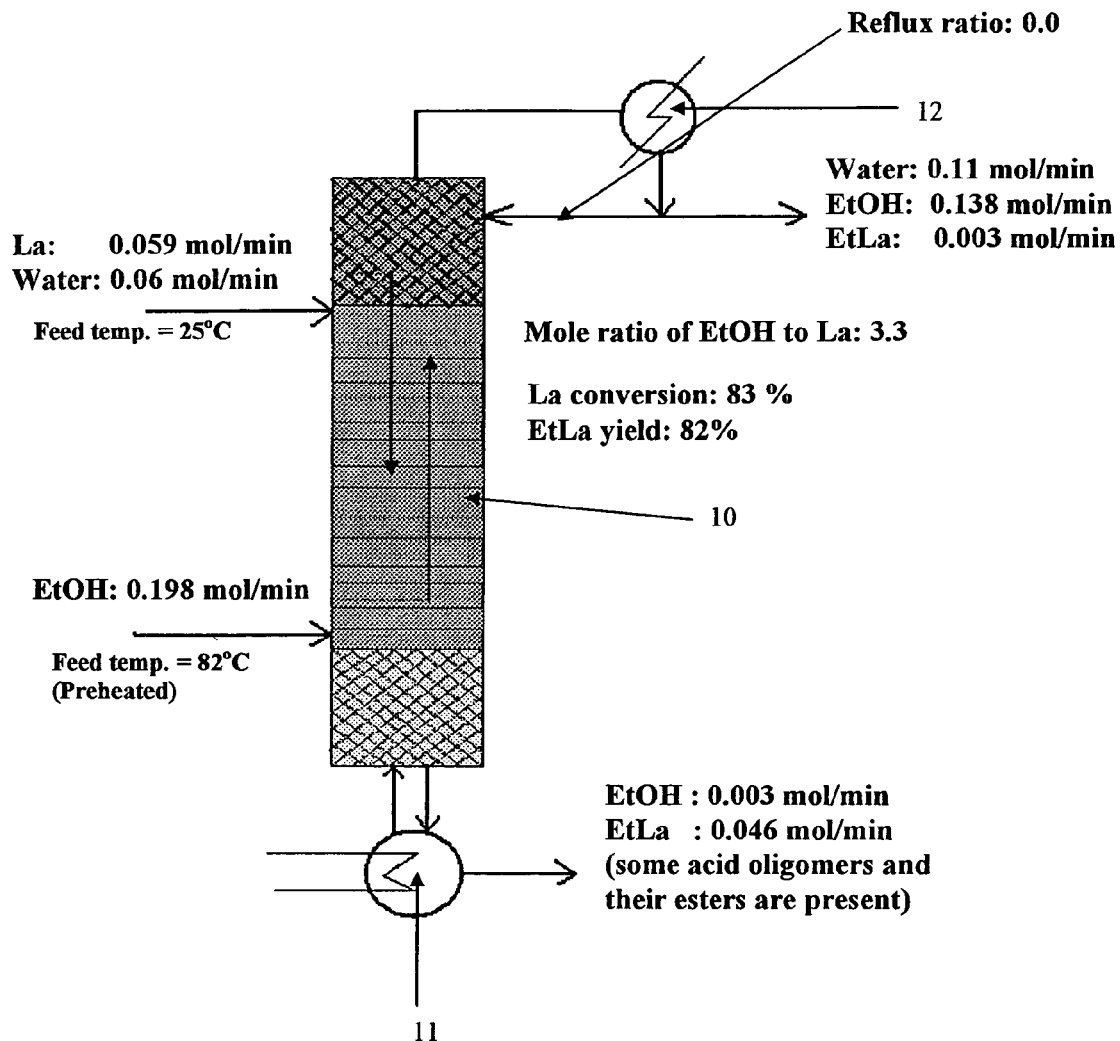
FIG. 1 is a representative result from the Bench-Scale run for ethyl lactate production from 85 wt % aqueous lactic acid solution and absolute ethanol as reactant feed.

All patents, patent applications, government publications, government regulations, and literature references cited in this specification are hereby incorporated herein by reference in their entirety. In case of conflict the present description, including definitions, will control.

The improved process to make organic acid esters via reactive distillation is simple, inexpensive, and does not create large quantities of waste. The process is unique and has several advantages that distinguish it from prior methods for making esters. First, the use of a reactive distillation column is less expensive than the conventional batch process because it is a continuous process and because an unsoluble acidic ion exchange resin in structured packing elements is used as a catalyst instead of a soluble mineral acid. The ester formation and purification of the product can take place in a single piece of equipment, whereas a conventional process may require up to ten separate pieces of equipment. This reactive distillation process avoids the inherent difficulties associated with membrane processes. The process does not require external heating of the column.

The mode of operation of the reactive distillation column is different from that used to make methyl and ethyl acetate, and acetate esters because the relative volatilities of the lactate esters, water, and alcohols are different than with acetates. In an acetate formation column, the acetate ester product is removed at the top of the column and water exits at the bottom. In the present invention as applied to organic acids such as lactic acid, propionic acid, and others, the ester product exits at the bottom of the column and water is distilled off at the top along with the extra alcohol. The ester product is refluxed to heat the column.

The prior art on fatty acid esterification describe a reactive distillation column mode of operation similar to the present invention, but pure organic acid feeds are usually used as feedstocks. The present invention uses acids fed in an aqueous solution in an amount of 10 to 80% by weight water.

The reactive distillation process has an advantage over existing processes for producing organic acid esters, in that transesterification reactions can be carried out in the reactive distillation column to produce different esters from a single parent ester. Methyl propionate can be produced as a parent ester via the reaction of methanol and propionic acid. Ethyl propionate can be produced via the reaction of methyl propionate with ethanol, or butyl propionate via reaction of methyl propionate with butanol. Any other propionate ester can likewise be produced in this way. The distinct advantage of this approach is that all of these reactions, including the original parent ester formation, can be carried out in the same piece of relatively inexpensive equipment. The ability to make a family of products using a single piece of equipment greatly improves process economics, provides better flexibility, and creates less risk than a process geared to produce a single product.

There exists a large potential market for converting biomass-based organic acids, produced by fermentation of corn- or other crop-derived sugars, to their ethyl esters from ethyl alcohol which is produced in the fermentates. These ethyl esters have the advantages of being nontoxic, effective as solvents, and "green" in that they are produced from renewable resources. The potential markets for esters such as ethyl lactate have been described (Watkins, K., Chemical & Engineering News 80(2), 15 (2002); and Formasari, G., Chimica e l'Industria (Milan) 82(1), 26 (2000)). Presently operating corn ethanol plants can be expanded to include production of organic acids and their esters. The total market for petrochemical based solvents is several billion 1 b/yr—esters could replace a substantial of these and thus have an annual market exceeding one billion pounds.

Figure 2:
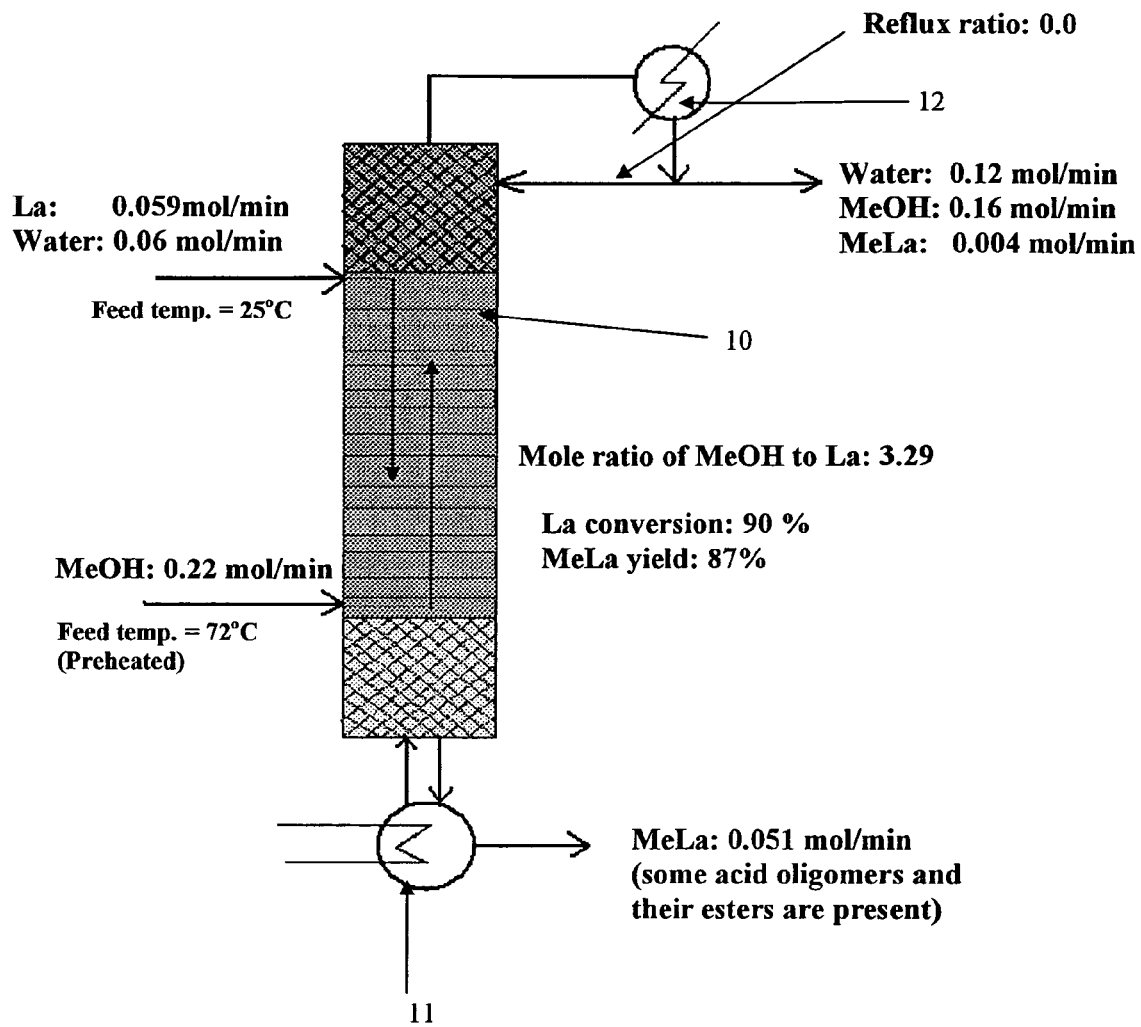
FIG. 2 is a representative result from the Bench-Scale run for methyl lactate production from 85 wt % aqueous lactic acid solution and absolute methanol as reactant feed.
Figure 3:
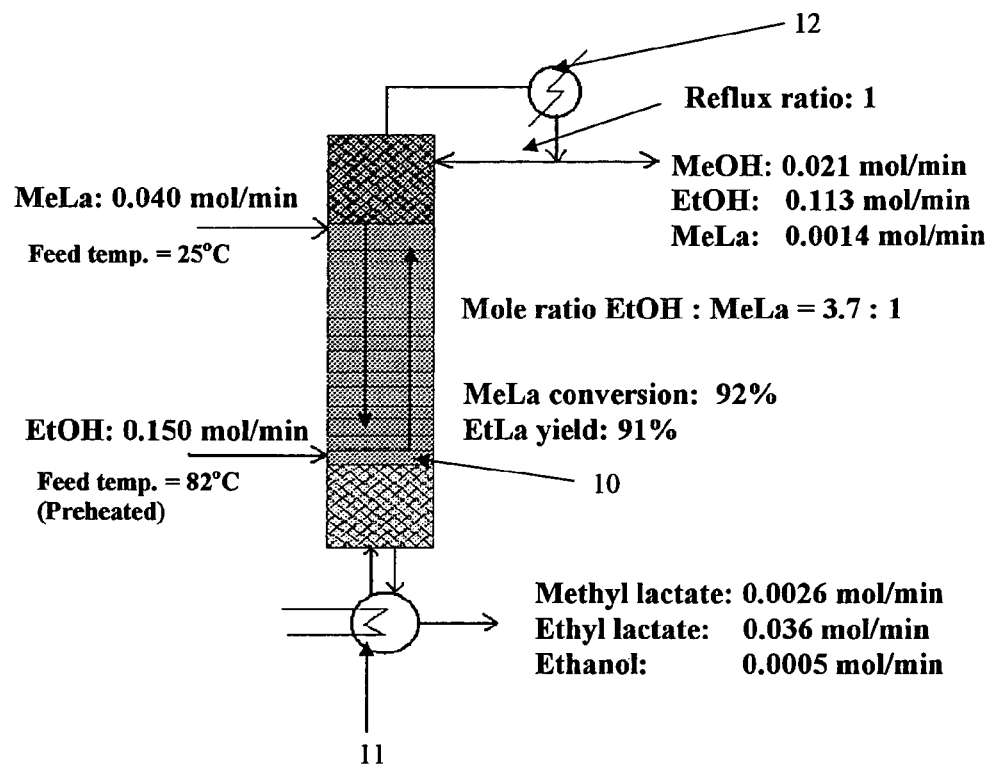
FIG. 3 is a representative result from the Bench-Scale run for ethyl lactate production from absolute methyl lactate and absolute ethanol as reactant feed.

The improved reactive distillation process is shown via examples of ethyl lactate and methyl lactate formation in FIGS. 1 to 3. FIG. 1 shows a scheme for the bench scale production (Example 5) of ethyl lactate in a process that consists of a single reactive distillation column 10 in which absolute ethanol or an ethanol/water mixture is fed near the bottom of the column and lactic acid solution in water is fed near the top of the column. Ethyl lactate product is generated and exits at the bottom of the column from a reboiler 11, either in a pure form or along with small quantities of ethanol. If present, ethanol can be easily separated from the product ester by simple distillation and recycled. At the top of the distillation column, water and excess ethanol exit and undergo treatment to recover using a condenser 12 and recycle unused ethanol via one of several means. If the reactive distillation process is integrated into an existing fuel ethanol production facility, the ethanol/water top product can easily be recycled back into the ethanol purification facility to recover the unused ethanol in pure form. Typically, this is accomplished by first distilling the ethanol to form an ethanol-water azeotrope and then using molecular sieves to break the ethanol-water azeotrope formed by distillation. In an alternate scheme, the ethanol-water azeotropic mixture can be directly recycled back to the reactive distillation column. This facilitates a reactive distillation process with feeding of azeotropic ethanol either alone or along with absolute ethanol at the same or at different feed positions along the reactive distillation column for production of ethyl lactate. In a third scheme, applicable for alcohols which do not form azeotropes with water, a second distillation column can be used to separate the excess alcohol from water and recycle it back to the column feed. FIG. 2 (Example 10) shows a representative example of bench scale methyl lactate production.

FIG. 3 shows a representative bench scale transesterification (Example 12) in the same column 10. Ethanol and methanol are shown as example alcohols. Alcohols greater than C4 are less volatile and therefore are less likely to be used.

Reactive Distillation Experiments

Equipment and methods: Reactive distillation experiments were conducted in laboratory and pilot scale facilities. The reactive distillation columns consist of Pyrex tubes 5.0 cm in diameter and 2.0 m in height for the laboratory-scale column 10 and up to 6.0 meters in height for the pilot-scale column. The columns were equipped with feed ports at different points along their length to accommodate both acid and alcohol feed streams; ports not used for feed streams were equipped with thermocouples to monitor column temperature over the course of reaction. The columns were fitted with Katapak-SP catalytic structured packing from Sulzer, Inc. (Pasadia, Tex. and Winterthur, Switzerland) or Katamax catalytic structured packing from Koch-Glitsch, Inc. (Wichita, Kans.). The preferred structure is shown in U.S. Pat. No. 5,470,542 to Sulzer, Inc. The packing contained 75 g AMBERLYST 15™ Rohm & Haas, Philadelphia, Pa.) strong cationic exchange resin per meter of height as catalyst. AMBERLYST 15™ is a sulfonic acid macroreticular ion exchange resin. The column was also outfitted with a one-liter reboiler flask 11 and condenser 12 with reflux splitter to facilitate designation of reflux ratio. The system also included separate feed pumps for alcohol and acid.

Products from reactive distillation were analyzed by one of several methods. Alcohol, water, and ester products were identified and quantified by gas chromatography using a Varian 3700™ (Palo Alto, Calif.) gas chromatograph equipped with a PORAPAK Q (Alltech, Inc., Deerfield, Ill.) column and a thermal conductivity detector. Acetonitrile was used as an internal standard to facilitate quantitative analysis. Lactic acid concentration was determined by direct titration of bottoms stream using NaOH. Outlet and feed concentrations were placed into an EXCEL™ spreadsheet to allow calculation of overall product purities, conversion of lactic acid, and to facilitate an overall material balance on the column.

EXAMPLES 1 TO 8

Bench-scale ethyl lactate formation. The following experiments in Examples 1 to 8, involve lactic acid and alcohols, using the bench-scale reactive distillation process for producing organic acid esters of the present invention.

Ethyl Lactate Formation: In the reactive distillation process for ethyl lactate formation, absolute ethanol or azeotropic ethanol was fed near the bottom of the column and lactic acid solution in water was fed near the top of the column. Ethyl lactate was generated in the reactive zone of the distillation column and exited at the bottom of the column. Depending on the feed compositions, ethyl lactate sometimes contained a small quantity of ethanol and water that was easily separated by simple distillation and recycled. Water and excess ethanol exited at the top of the column. If the reactive distillation process was integrated into an existing ethanol production facility, the ethanol/water top product can be recycled back into the process to recover the unused ethanol in absolute form. Alternatively, both recycled azeotropic and absolute ethanol can be fed into the column either at the same or at different locations of the reactive distillation column to produce ethyl lactate.

Experiments performed for ethyl lactate formation are given in Table 1; a schematic of the reactant and product flow for a typical experiment (Example 5) is given in FIG. 1. Absolute ethanol was fed at the bottom of the reactive distillation column reactive zone and lactic acid solution at the top of the reactive zone. Ethanol and water were collected at the top of the column and ethyl lactate with unreacted lactic acid were collected from the column reboiler. A small quantity of ethyl lactate was observed in the distillate stream for some experiments, but that loss was overcome by optimizing column operation. The highest lactic acid conversion observed was 83% (Example 5); this number is significant for a relatively short distillation column and is much higher than the equilibrium lactic acid conversion (~55%) at the same temperature. This conversion was achieved without reflux and with lactic acid fed very near the top of the column; thus the column was operated essentially as a reactive stripping column. Reasonable purity of ethyl lactate (80 mol %) was observed from the small column—with the majority of impurity being unreacted lactic acid and small quantities of ethanol and water. A taller column, where additional conversion of lactic acid and better stripping of ethanol and water can be achieved, provides a bottoms product of essentially pure ester.

It should be noted that Examples 5-8 in Table 1 were conducted by preheating the ethanol feed to an elevated temperature (82° C.) where it is vaporized. This results not only in reduced reboiler duty but in a lower water content in the bottom product. Ethanol preheating has a beneficial effect in column operation.

TABLE 1

Esterification of Lactic acid with Ethanol

| Ex | Aq. LA Feed comp. Wt % | LA feed rate Mol/min | EtOH feed rate Mol/min | $H_2O$ feed rate Mol/min | EtOH:LA Molar ratio | Reflux ratio (L/D) | % LA conv. | Bottom product mole composition (%) | | | |
|---|---|---|---|---|---|---|---|---|---|---|---|
| | | | | | | | | $H_2O$ | EtOH | EtLa | La |
| 1 | 20 | 0.014 | 0.1288 | 0.28 | 9.2 | 0.42 | 19 | 72 | 25 | 0.5 | 2.5 |
| 2 | 85 | 0.092 | 0.097 | 0.093 | 1.05 | 0 | 61 | 16 | 2 | 50 | 31 |
| 3 | 85 | 0.07 | 0.13 | 0.071 | 1.91 | 0 | 71 | 5 | 2 | 67 | 26 |
| 4 | 85 | 0.071 | 0.18 | 0.0725 | 2.52 | 0 | 76 | 3 | 6 | 72 | 18 |
| 5 | 85 | 0.05 | 0.19 | 0.06 | 3.89 | 0 | 85 | 2 | 4 | 80 | 14 |
| 6 | 85 | 0.049 | 0.195 | 0.05 | 3.96 | 0.2 | 81 | 1.8 | 4 | 79 | 15 |
| 7 | 85 | 0.049 | 0.195 | 0.05 | 3.96 | 0.5 | 68 | 2.5 | 5.6 | 67 | 28 |
| 8 | 85 | 0.045 | 0.19 | 0.05 | 3.89 | 2.33 | 37 | 47 | 18 | 14 | 20 |

LA = lactic acid;
EtOH = ethyl alcohol;
EtLa = ethyl lactate.
L = Liquid recycled to the column.
D = Distillate Product.

EXAMPLES 9 AND 10

Methyl lactate formation: The formation of methyl lactate in the laboratory scale reactive distillation column was studied in much the same fashion as in ethyl lactate formation. Results of experiments conducted are given in Table 2; a schematic of a typical experiment (Example 10) is given in FIG. 2.

TABLE 2

Esterification of Lactic acid with Methanol

| Ex | Aq. LA Feed comp. Wt % | LA feed rate Mol/min | $H_2O$ feed rate Mol/min | MeOH feed rate Mol/min | MeOH:LA Molar ratio | Reflux ratio (L/D) | % LA conv. | Bottom product mole composition (%) | | | |
|---|---|---|---|---|---|---|---|---|---|---|---|
| | | | | | | | | $H_2O$ | MeOH | MeLa | La |
| 9 | 20 | 0.014 | 0.28 | 0.168 | 10.13 | 0.5 | 46 | 66 | 30 | 1.39 | 1.34 |
| 10 | 85 | 0.059 | 0.06 | 0.22 | 3.29 | 0 | 90 | 0 | 0 | 91.5 | 8.5 |

MeLA = methyl lactate

Methanol and water were produced at the top of the distillation column, and methyl lactate along with unreacted lactic acid was produced at the bottom of the column. Again, a slight amount of methyl lactate was observed in the distillate stream in some cases. A lactic acid conversion as high as 90% was observed experimentally.

The primary advantage of producing methyl lactate over ethyl lactate is that methanol and water do not form an azeotrope. Thus, the methanol-water mixture produced at the top of the reactive distillation column was separated by simple, low temperature distillation and the methanol recycled to the column. In this way, only a stoichiometric quantity of methanol is consumed in the esterification and the overall processing costs are lower.

EXAMPLES 11 AND 12

Trans-esterification of methyl lactate to ethyl lactate: The ability to produce methyl lactate straightforwardly by reactive distillation opens an additional pathway to lactate ester formation—that of transesterification. The advantage of transesterification reactions is that there is no water produced or required in the system, thus hydrolysis of the esters is not a concern. To explore this route, several transesterification experiments were conducted in the lab scale reactive distillation column. In transesterification, methyl lactate was fed at the top of the column reactive zone and ethanol is fed at the bottom of the reactive zone. Ethanol moved up the distillation column and reacted with methyl lactate to give ethyl lactate and methanol. All methanol and excess ethanol exited at the top of the column, and ethyl lactate, unreacted methyl lactate, and a small quantity of ethanol were removed continuously from the reboiler.

Results of the transesterification of methyl lactate to ethyl lactate are shown in Table 3 in Examples 11 and 12 (Example 12 is in FIG. 3). A methyl lactate conversion of 94% was achieved with an ethyl lactate purity in the bottoms stream exceeding 90% by weight. Thus it is clear that transesterification is a viable method for producing a family of organic acid esters from a single parent ester. In a larger column complete transesterification will take place with pure product formation.

TABLE 3

Transesterification of Methyl lactate with Ethanol

| Ex | MeLa Feed comp. Wt % | MeLa feed rate Mol/min | EtOH feed rate Mol/min | EtOH:Mela Molar ratio | Reflux ratio (L/D) | % MeLa conv. | Bottom product mole composition (%) | | | |
|---|---|---|---|---|---|---|---|---|---|---|
| | | | | | | | EtOH | MeOH | MeLa | EtLa |
| 11 | 100 | 0.06 | 0.138 | 2.27 | 0.42 | 84 | 47 | 0 | 9.6 | 43 |
| 12 | 100 | 0.04 | 0.15 | 3.75 | 1 | 94 | 1.18 | 0 | 6.18 | 92.6 |

EXAMPLES 13 to 16

Process Simulations

Computer simulations of the reactive distillation process for ester formation using ASPENPLUS™ Version 11.1 and 11.2 (Aspen Technology Inc., Cambridge Mass.) process simulation software. Using ASPENPLUS™, the performance of the laboratory bench scale column was simulated on the computer using the equilibrium stage model with a height of an equivalent theoretical plate (HETP) equal to 0.6 meters of packing was simulated. From this, the parameter values that gave the best depiction of the actual process were identified. Those same parameter values were used to simulate a commercial-scale esterification process at a production rate for ethyl lactate at 25 million pound per year (13.88 mol/min). Results of those simulations are given in Table 4 for several monomeric lactic acid feed compositions. It is seen that feed solutions having a high acid content were readily converted to esters in high yields. As monomer acid concentration in the aqueous feed stream is reduced, it is necessary to add larger quantities of alcohol in order to maintain high acid conversion. As a consequence, the quantity of ethanol in the bottoms increases with increasing ethanol feed rate. It should be noted that, in the simulation, both lactic acid solution and ethanol were fed to the column as liquids at room temperature (298° K.). The state of the feed clearly influences both reboiler duty and the quantity of ethanol and water in the bottoms product.

There is an opportunity to reduce ethanol content in the bottoms via preheating the feed streams (Examples 5-8). Even without exploiting additional possibilities, the simulations demonstrate that the process can be used to esterify organic acids in relatively dilute aqueous solutions and achieve high yields of the ester product.

TABLE 4

Results of Simulation studies of Commercial-Scale Lactic acid esterification with Ethanol

| Ex | Aq. LA Feed comp. Wt % LA | LA feed rate Mol/min | H₂O feed rate Mol/min | EtOH feed rate Mol/min | EtOH:LA Molar ratio | # stages (N) | Reflux ratio (L/D) | % LA conv. | Bottom product mole composition (%) | | | |
|---|---|---|---|---|---|---|---|---|---|---|---|---|
| | | | | | | | | | H₂O | EtOH | EtLa | La |
| 1 | 20 | 13.88 | 278.05 | 416.66 | 30 | 42 | 0.01 | 99 | 0.099 | 92.36 | 7.525 | 0.00 |
| 2 | 30 | 13.88 | 162.22 | 277.77 | 20 | 42 | 0.01 | 99 | 0.099 | 90.17 | 9.721 | 0.00 |
| 3 | 50 | 13.88 | 69.72 | 111.11 | 8 | 42 | 0.01 | 99 | 0.097 | 71.30 | 28.57 | 0.01 |
| 4 | 70 | 13.88 | 29.72 | 55.55 | 4 | 40 | 0.01 | 99 | 0.252 | 21.62 | 77.82 | 0.29 |

Abbreviations:
Aq. = aqueous;
Comp. = composition;
Conv. = conversion;
LA = lactic acid;
EtOH = ethanol;
MeOH = methanol;
EtLa = ethyl lactate;
MeLa = methyl lactate;
H₂O = water Table 5 provides a summary of the simulated commercial-scale column configurations for esterification of a 70 wt % lactic acid solution with absolute ethanol and methanol in a 3:1 alcohol:lactic acid ratio, and for transesterification of pure methyl lactate with absolute ethanol. It is seen that simulation predicts reasonably-sized commercial scale columns for producing organic acid esters.

TABLE 5

Commercial scale column configurations for esterification

| | Ethyl lactate (Ethanol + lactic acid) | Methyl lactate (Methanol + lactic acid) | Ethyl lactate (Methyl lactate + ethanol) |
|---|---|---|---|
| No. Of stages | 40 | 50 | 35 |
| Feed locations | 2 and 35 | 3 and 40 | 2 and 33 |
| Reactive stages | 7 to 35 | 8 to 40 | 11 to 33 |
| Reflux ratio | 0.001 | 0.001 | 5 |
| Boil-up ratio | 5 | 4.5 | 4 |

TABLE 5-continued

Commercial scale column configurations for esterification

|  | Ethyl lactate (Ethanol + lactic acid) | Methyl lactate (Methanol + lactic acid) | Ethyl lactate (Methyl lactate + ethanol) |
|---|---|---|---|
| Column height | 22 meter | 23 meter | 20 meter |
| Column diameter | 1 meter | 1 meter | 1.3 meter |

Abbreviations: Aq. = aqueous; Comp. = composition; Conv. = conversion; LA = lactic acid; EtOH = ethanol; MeOH = methanol; EtLa = ethyl lactate; MeLa = methyl lactate; $H_2O$ = water.

EXAMPLES 17 AND 18

Pilot-Scale Experiments and Simulation

Pilot-scale reactive distillation studies were conducted for the production of ethyl lactate. The column was configured such that the stripping zone constitutes the bottom 0.7 m of the column while the rectifying occupied the top 0.9 m below the condenser. The reactive zone thus made up the center 2.9 meters of the column. The column was assumed to contain a total of equilibrium 10 stages including reboiler and condenser. Lactic acid solution (~58 wt % monomer) was fed at the $2^{nd}$ stage (0.3 m below condenser) and absolute ethanol was fed at the $9^{th}$ stage (0.3 m above reboiler); both feeds were at room temperature (298° K).

As with the bench-scale column, a reflux ratio of zero was found to give the best overall conversion of lactic acid to ethyl lactate. Following several shakedown runs, a set of conditions were identified that give 81% lactic acid conversion to ethyl lactate. This value is similar to the conversion obtained after limited optimization in the bench-scale column. With further optimization of the pilot-scale column (see results of simulation below) conversions exceeding those in the bench-scale column can be achieved.

Figure 4:
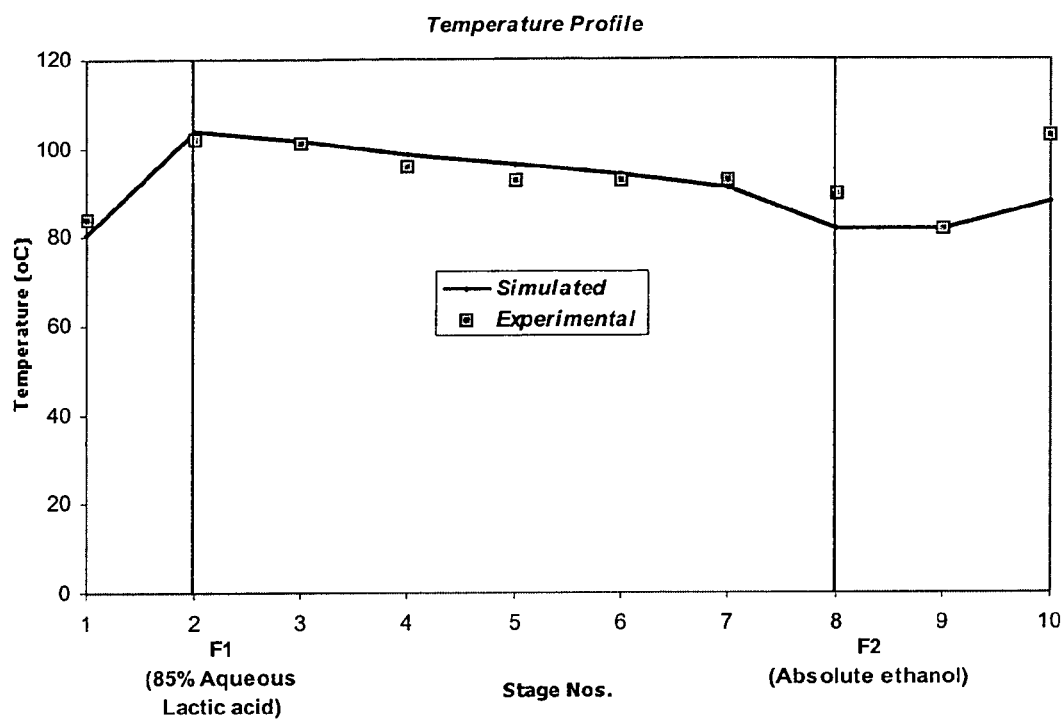
FIG. 4 is a graph of temperature profiles in pilot-scale column.
Figure 5:
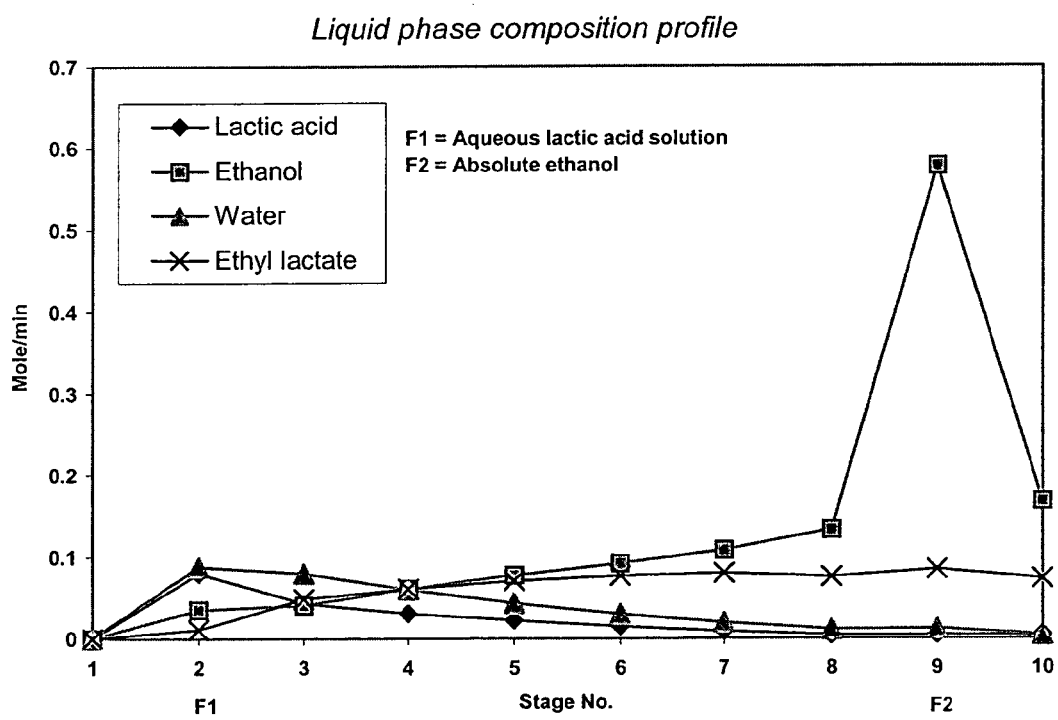
FIG. 5 is a graph of liquid-phase compositions from pilot-scale column simulation.

The pilot-scale reactive distillation column was simulated at reaction conditions and using the experimental reaction equilibrium data obtained in the laboratory scale column. The equilibrium stage model with an HETP of 0.6 m was used for the simulation. A comparison of the experimental and simulated results is given in Table 6 (Examples 17 and 18) below; there is reasonably good agreement between the product stream compositions and overall lactic acid conversion. Temperatures and stage-by-stage compositions for both simulations and experiments are given in FIGS. 4 and 5, respectively.

TABLE 6

Experimental and simulated results for pilot scale column

|  | Experimental | Simulation |
|---|---|---|
| Aq. Lactic acid feed rate | 0.081 mol/min | 0.081 mol/min |
| Water feed rate | 0.083 mol/min | 0.083 mol/min |
| Absolute Ethanol feed rate | 0.39 mol/min | 0.39 mol/min |
| Mole ratio of Ethanol to Lactic acid | 4.76 | 4.76 |
| No. of stages | 10 | 10 |
| Reactive stages | 3 to 8 | 3 to 8 |
| Feed position F1 (aq. Lactic acid) | $2^{nd}$ stage | $2^{nd}$ stage |
| Feed position F2 (absolute ethanol) | $9^{th}$ stage | $9^{th}$ stage |
| F1 feed temperature | 298 K | 298 K |

TABLE 6-continued

Experimental and simulated results for pilot scale column

|  | Experimental | Simulation |
|---|---|---|
| F2 feed temperature | 298 K | 298 K |
| Column diameter | 50 mm | 50 mm |
| Column height | 4.5 m | 4.5 m |
| Reflux ratio | 0 | 0.00001 |
| % Lactic acid conversion | 81% | 90% |
| $X_D$ (Lactic acid) | 0.00 | 0.009 |
| $X_D$ (Ethanol) | 0.46 | 0.48 |
| $X_D$ (Water) | 0.52 | 0.50 |
| $X_D$ (Ethyl lacate) | 0.006 | 0.007 |
| $X_B$ (Lactic acid) | 0.07 | 0.01 |
| $X_B$ (Ethanol) | 0.54 | 0.67 |
| $X_B$ (Water) | 0.12 | 0.01 |
| $X_B$ (Ethyl lactate) | 0.25 | 0.29 |

Additional simulations of the pilot-scale column were conducted by varying several operating parameters such as feed temperature, reboiler duty, feed flow rate and mole ratio. At optimal conditions, a lactic acid conversion of 92% was achieved with an ethyl lactate product purity of 84% by weight.

EXAMPLES 19 TO 40

In the following Examples 19 to 40 the pilot-scale column was operated as shown in Table 7. The column configuration in Table 7 is compared to the bench scale apparatus. The results are shown in Tables 8, 9 and 10.

TABLE 7

Column configurations for Bench-Scale and Pilot-Scale:

| Parameters | Bench-Scale Column | Pilot-Scale Column |
|---|---|---|
| Column height | 2 meter | 4.5 meter |
| Column diameter (internal) | 0.05 meter | 0.05 meter |
| Column packing | Katapak-Sulzer | Katapak-Sulzer |
| Catalyst inside packing | Amberlyst-15 | Amberlyst-15 |
| Enriching section (non-reactive) | 0.15 meter | 0.9 meter |
| Reactive section | 1.7 meter | 2.6 meter |
| Stripping section (non-reactive) | 0.15 meter | 0.7 meter |
| F1 | 0.075 meter below condenser | 0.14 meter below condenser |
| F2 (a) | 0.075 meter above reboiler | 0.08 meter above reboiler |
| (b) |  | 0.98 meter above reboiler |
| HETP | 0.6 meter | 0.6 meter |

TABLE 8

| Ex. | Aq. LA Feed Comp. | LA. Feed rate (M + D) Mol/min | EtOH Feed Comp | EtOH feed rate Mol/min | H₂O feed rate Mol/min | EtOH Feed temp. (° C.) | EtOH:LA Molar ratio | Reflux ratio | % Acid Conversion | A | B | Bottom Product composition (wt %) | | | |
|---|---|---|---|---|---|---|---|---|---|---|---|---|---|---|---|
| | | | | | | | | | | | | H₂O | EtOH | EtLa | C |
| 19 | 85% | 0.095 | 100% | 0.345 | 0.06 | 25 | 3.60 | 0.00 | 95.52 | 67.23 | 112.44 | 0.00 | 25.04 | 52.31 | 22.65 |
| 20 | 85% | 0.095 | 100% | 0.245 | 0.06 | 25 | 2.52 | 0.00 | 94.32 | 68.12 | 107.31 | 0.00 | 6.42 | 63.80 | 29.77 |
| 21 | 85% | 0.095 | 100% | 0.145 | 0.06 | 25 | 1.44 | 0.00 | 90.23 | 59.89 | 94.34 | 0.00 | 0.53 | 66.57 | 32.89 |
| 22 | 85% | 0.095 | 100% | 0.345 | 0.06 | 78 (liq) | 3.60 | 0.00 | 94.19 | 65.62 | 103.33 | 0.00 | 6.04 | 66.09 | 27.86 |
| 23 | 85% | 0.095 | 100% | 0.345 | 0.06 | 85 (vap) | 3.60 | 0.00 | 94.93 | 61.30 | 96.53 | 0.00 | 0.73 | 67.30 | 31.96 |
| 24 | 85% | 0.095 | 100% | 0.345 | 0.06 | 25 | 3.60 | 0.20 | 87.58 | 66.23 | 104.30 | 0.06 | 32.45 | 45.48 | 21.91 |
| 25 | 85% | 0.095 | 100% | 0.345 | 0.06 | 25 | 3.60 | 0.50 | 76.64 | 54.03 | 85.08 | 0.19 | 41.49 | 34.96 | 23.36 |
| 26 | 85% | 0.095 | 100% | 0.345 | 0.06 | 25 | 3.60 | 1.00 | 55.90 | 44.14 | 69.50 | 0.92 | 44.88 | 25.03 | 29.17 |

EtOH Feed position above the reboiler = 0.09 m
Lactic acid feed temperature = 25° C.
A: Yield of ethyl lactate based on total lactic acid including monomer & dimer
B: Yield of ethyl lactate based on lactic acid monomer present in feed
C: A mixture consisting of ethyl ester of dimeric, trimeric lactic acid, as well as unreacted lactic acid monomer & dimer and higher oligomers and their esters

TABLE 9

| Ex. | Aq. LA Feed Comp. | LA. Feed rate (M + D) Mol/min | EtOH Feed Comp | EtOH feed rate Mol/min | H₂O feed rate Mol/min | EtOH Feed temp. (° C.) | EtOH:LA Molar ratio | Reflux ratio | % Acid Conversion | A | B | Bottom Product composition (wt %) | | | |
|---|---|---|---|---|---|---|---|---|---|---|---|---|---|---|---|
| | | | | | | | | | | | | H₂O | EtOH | EtLa | C |
| 27 | 85% | 0.095 | 100% | 0.345 | 0.06 | 25 | 3.60 | 0.00 | 93.61 | 64.67 | 101.83 | 0.00 | 25.20 | 50.80 | 23.94 |
| 28 | 85% | 0.095 | 100% | 0.345 | 0.06 | 25 | 3.60 | 0.50 | 78.01 | 63.57 | 100.10 | 0.20 | 44.27 | 38.19 | 17.34 |
| 29 | 85% | 0.095 | 95% | 0.36 | 0.113 | 25 | 3.70 | 0.00 | 81.51 | 65.10 | 102.52 | 4.33 | 38.09 | 41.87 | 15.71 |
| 30 | 85% | 0.095 | 95% | 0.36 | 0.113 | 85 (Vap) | 3.70 | 0.00 | 85.40 | 57.73 | 90.91 | 0.21 | 0.43 | 62.16 | 37.20 |
| 31 | 85% | 0.095 | 100% | 0.345 | 0.06 | 25 | 3.73 | 0.00 | 93.37 | 67.95 | 107.01 | 0.67 | 22.08 | 57.03 | 20.20 |

EtOH Feed position above the reboiler = 1.00 m
Lactic acid feed temnerature = 25° C.
Run 13: Catalyst in reboiler
A: Yield of ethyl lactate based on total lactic acid including monomer & dimer
B: Yield of ethyl lactate based on lactic acid monomer
C: A mixture consisting of ethyl ester of dimeric, trimeric lactic acid, as well as unreacted lactic acid monomer & dimer and higher oligomers and their esters

TABLE 10

| Ex. | Aq. LA Feed Comp. | LA. Feed rate (M + D) Mol/min | EtOH Feed Comp | EtOH feed rate Mol/min | H₂O feed rate Mol/min | LA Feed temp. (° C.) | EtOH Feed temp. (° C.) | EtOH:LA Molar ratio | % Acid Conversion | A | B | Bottom Product composition (wt %) | | | |
|---|---|---|---|---|---|---|---|---|---|---|---|---|---|---|---|
| | | | | | | | | | | | | H₂O | EtOH | EtLa | C |
| 32 | 50% | 0.05 | 100% | 0.37 | 0.25 | 25 | 25 | 7.28 | 50.56 | 53.78 | 58.82 | 5.87 | 60.82 | 18.18 | 15.11 |
| 33 | 50% | 0.048 | 100% | 0.349 | 0.25 | 25 | 25 | 7.14 | 56.84 | 56.81 | 67.33 | 3.11 | 62.11 | 20.93 | 13.78 |
| 34 | 50% | 0.048 | 100% | 0.349 | 0.25 | 100 | 25 | 7.14 | 66.17 | 65.96 | 78.18 | 1.22 | 61.55 | 25.45 | 11.79 |
| 35 | 50% | 0.05 | 100% | 0.454 | 0.25 | 100 | 85 (Vap) | 9.3 | 93.99 | 68.61 | 81.31 | 0.00 | 19.61 | 61.50 | 18.88 |
| 36 | 50% | 0.048 | 100% | 0.349 | 0.25 | 100 | 85 (Vap) | 7.14 | 94.82 | 60.64 | 71.87 | 0.00 | 0.00 | 70.94 | 29.06 |
| 37 | 50% | 0.05 | 100% | 0.35 | 0.25 | 25 | 85 (vap) | 7.31 | 90.91 | 65.21 | 82.14 | 0.22 | 3.09 | 72.22 | 24.45 |
| 38 | 50% | 0.048 | 100% | 0.25 | 0.25 | 25 | 85 (vap) | 5.3 | 86.07 | 66.43 | 84.16 | 0.01 | 0.05 | 69.36 | 30.56 |
| 39 | 50% | 0.05 | 100% | 0.25 | 0.25 | 25 | 78 (Liq) | 5.3 | 74.11 | 63.86 | 82.89 | 0.03 | 17.63 | 57.72 | 24.59 |

TABLE 10-continued

| Ex. | Aq. LA Feed Comp. | LA. Feed rate (M + D) Mol/Min | EtOH Feed Comp | EtOH feed rate Mol/min | H₂O feed rate Mol/min | LA Feed temp. (° C.) | EtOH Feed temp. (° C.) | EtOH:LA Molar ratio | % Acid Conversion | A | B | Bottom Product composition (wt %) | | | |
|---|---|---|---|---|---|---|---|---|---|---|---|---|---|---|---|
| | | | | | | | | | | | | H₂O | EtOH | EtLa | C |
| 40 | 50% | 0.048 | 100% | 0.45 | 0.25 | 25 | 85 (Vap) | 9.22 | 89.61 | 71.40 | 88.12 | 0.02 | 29.34 | 58.43 | 12.19 |

EtOH Feed position above the reboiler = 1.00 m
Reflux ratio = 0.00
A: Yield of ethyl lactate based on total lactic acid including monomer & oligomers
B: Yield of ethyl lactate based on lactic acid monomer
C: A mixture consisting of dimeric, trimeric, and higher oligomers of lactic acid and their ethyl esters, as well as unreacted lactic acid monomer 1. Parameters in Example 19 were fixed as best optimized reaction parameters for the current process. Various different parameters were altered in subsequent experiments to study their effect on process performance and results were compared with that from Example 19.

2. Examples 19 to 26 (Table 8) were performed by feeding ethanol near the bottom of the stripping section, i.e. 0.09 m above the reboiler; while Examples 27 to 40 (Tables 9 and 10) were performed by feeding ethanol near the bottom of the reactive zone, i.e. 1 m above the reboiler.

3. Examples 19 to 28 & 31 to 40 were performed by feeding absolute ethanol; while Examples 29 and 30 were performed by feeding a mixture of 95 wt % ethanol and 5 wt % water.

4. Examples 19 to 21 illustrate the effect of ethanol:lactic acid mole ratio. As the mole ratio of ethanol to lactic acid decreased from 3.60 to 1.44, overall yield of ethyl lactate decreased from 67% to 59%, which is due to decrease in ethanol concentration in reactive zone; but at the same time the bottoms product at low ethanol:lactic acid feed ratios is almost free from water and ethanol and makes the separation of final product much simpler in one distillation column.

5. Examples 19, 22 and 23 illustrate the effect of ethanol feed temperature. Increasing ethanol feed temperature from 25° C. to 78° C. (liquid) and then up to 85° C. (vaporized) has a deleterious effect on yield of ethyl lactate even though water and ethanol concentration in reboiler and thus bottoms stream are at their lowest level facilitating ease of separation of ethyl lactate from the mixture. Results from Example 21 (liquid ethanol feed) and Example 23 (vaporized ethanol) are comparable. It can be observed that in both the cases of lower ethanol mole ratio and vaporized ethanol feed, the ethanol concentration in reactive zone is less than in Example 19 and this has a favorable impact on maintaining lower ethanol concentration in reboiler, albeit with some loss in overall conversion and yield.

6. Examples 19 and 24 to 26 illustrate the effect of reflux ratio. As the reflux ratio was increased from 0 to 0.2 and subsequently to 0.5 & 1, a decrease in overall lactic acid conversion as well as ethyl lactate yield was observed. Increasing reflux ratio results in higher water concentration in the reactive zone, hence thereby reducing the conversion of lactic acid.

7. Examples 19 and 27 illustrate the effect of ethanol feed location (i.e. 0.09 m above reboiler for Example 19 and 1 m for Example 27). Ethanol feed points were altered to observe the effect of stripping section length on ethanol fractionation. No significant difference in results obtained from Example 19 and Example 27 was observed.

Therefore subsequent Examples from 28 to 40 were performed by keeping the ethanol feed point at 1 m above the reboiler.

8. Examples 27 and 28 illustrate the effect of reflux ratio. As the reflux ratio was increased from 0 to 0.5, a decrease in lactic acid conversion as well as ethyl lactate yield was observed. These observations are similar as those obtained with the same set of reflux ratios for ethanol feed 0.09 m above the reboiler (Examples 19 and 25).

9. Examples 27 and 29 illustrate the effect of ethanol feed composition. Ethanol feed composition was varied between absolute ethanol (Example 27) and azeotropic composition of ethanol and water (Example 29). Feeding water along with ethanol decreases lactic acid conversion and increases in the water concentration in reboiler and bottoms stream.

10. Examples 29 and 30 illustrate the effect of ethanol feed temperature when azeotropic ethanol feed was used. Azeotropic ethanol was fed in its vapor form to observe whether complete removal of water from the reboiler is possible. By vaporizing ethanol feed, water and ethanol concentrations in the reboiler and bottoms stream were lowered.

11. Examples 27 and 32 illustrate the effect of aqueous lactic acid feed composition. The most advantageous aspect about 85 wt % aqueous solution is minimum quantity of water associated with it, which helps in increasing lactic acid conversion. However, 85 wt % lactic acid contains dimer (lactoyllactic acid) and trimers (lactoyllactoyl lactic acid) and higher linear oligomers besides lactic acid monomer and this poses a significant challenge in obtaining high yields of ethyl lactate primarily due to the esterification of dimer (lactoyllactic acid) and trimer (lactoyllactoyl lactic acid) to their respective ethyl esters. It was thought beneficial to use 50% by weight lactic acid solution which contains a minimal amount of dimer (lactoyllactic acid) in order to increase overall yield of ethyl lactate. The mole ratio of ethanol to lactic acid used in Example 32 is 7.28:1.

Examples 32 to 40 were carried out with 50 wt % lactic acid solution.

12. Examples 33 and 34 illustrate the effect of lactic acid feed temperature. Lactic acid feed temperature was increased from 25° C. to 100° C.; a marked increase was observed in lactic acid conversion, yield of ethyl lactate and decrease in water content was also seen in reboiler.

13. Examples 33 and 35 illustrate the effect of ethanol to lactic acid molar feed ratio and ethanol feed temperature. Since positive effects were observed at higher lactic acid feed temperature, it was thought to increase the ethanol to lactic acid molar feed ratio from 7.14 to 9.3. Ethanol was fed in its vapor form and this enhanced lactic acid conversion and ethyl lactate yield. The most significant result was absence of water in the reboiler and bottoms stream, even though more diluted solution of lactic acid was used than in earlier examples 21 to 31.

14. Examples 35 and 36 illustrate the effect of ethanol to lactic acid feed ratio when both reactants are fed at higher temperature. Significant amount of ethanol was observed in reboiler in Example 35, therefore ethanol to lactic acid mole ratio was reduced to 7.14 from 9.3. By lowering ethanol feed rate and vaporizing it as well as feeding heated lactic acid solution, both ethanol and water were eliminated in the reboiler and bottoms streams, albeit with a modest decrease in ethyl lactate yield.

15. Examples 33 and 37 illustrate the effect of ethanol feed temperature at same feed rate. Increasing ethanol feed temperature from 25° C. to 85° C. (vaporized) had a positive effect on lactic acid conversion. The conversion of lactic acid increased from 56% (Example 33) to 91% (Example 37) and ethyl lactate yield increased as well. Feeding ethanol at its vapor temperature also greatly reduces the quantity of water and ethanol in the reboiler and bottoms streams.

16. Examples 37 and 38 illustrate the effect of ethanol feed rate at same feed temperature. Since a small amount of ethanol was observed in the reboiler in Example 37, the ethanol to lactic acid molar feed ratio was further decreased from 7.3 to 5.3. This decrease in ethanol feed rate further decreases ethanol and water in the reboiler and bottoms streams, albeit with slightly lower lactic acid conversion and ethyl lactate yield.

17. Examples 38 and 39 illustrate the effect of ethanol feed temperature at same feed rate. It was assumed that feeding ethanol at a lower rate in its vaporized state might result in lower ethanol concentration in the reactive zone, which in turn would explain lower lactic acid conversion and ethyl lactate yield. In Example 39, ethanol was fed as a saturated liquid at 78° C. This resulted in substantial quantity of ethanol in the reboiler and bottoms streams. A lower conversion of lactic acid was also observed although yield of ethyl lactate remained comparable to that in Example 38.

18. Examples 37, 38 and 40 illustrate the effect of ethanol to lactic acid molar feed ratio at the same feed temperature. When ethanol mole ratio was decreased from 7.31 (Example 37) to 5.3 (Example 38), a negligible amount of ethanol was seen in reboiler with some loss in lactic acid conversion and ethyl lactate yield. Upon increasing ethanol to lactic acid molar feed ratio to 9.2 (Example 40), ethyl lactate yield is enhanced but a substantial quantity of ethanol appears in the reboiler and bottoms stream.

The person of skill in the art would recognize that the present invention can be applied to esterify organic acids besides lactic acid, including other biomass-derived acids such as succinic acid, propionic acid, malic, glutaric, adipic, glyceric, 3-hydroxy propanoic, citric, levulinic, and amino acids such as alanine, serine, glycine and lysine.

Lactic acid is unique in that it dimerizes and trimerizes in reactive distillation. The oligomer products of the process are useful as non-volatile solvents for paints and in paint removers. The solvents are considered to be "green".

EXAMPLE 41

Hydrolysis Experiment of Oligomers and Oligomer Esters

Hydrolysis experiment was performed with 37 g of residue, collected by completely removing ethyl lactate by vacuum distillation, and 37 g of water (to maintain the concentration of final solution in a range of 50 wt %). This residue contains monomer, dimer, and trimer lactic acid along with dimer and trimer ethyl esters. A reaction was performed in batch reactive distillation apparatus to remove the ethanol as it was formed during the hydrolysis reaction. A schematic of the reaction set-up is provided in FIG. 6. Reaction was catalyzed by AMBERLYST-15 ion exchange resin at a loading of 3 wt % of total weight of reaction mass. Reaction mixture was first allowed to reflux for 2 minutes before adding the catalyst and after adding the catalyst, periodic samples were collected to follow the concentration profile of reactants and products.

The reaction proceeded with hydrolysis of the ethyl ester of dimer lactoyllactic acid and trimer lactoyllactoyl lactic acid yielding ethanol. The reaction was allowed to proceed for 7 h and sample was analyzed for final concentration of lactic acid and dimer. All dimer and trimer esters were consumed along with all trimer acid. Lactic acid and dimer acid were determined by direct titration with NaOH and back titration of excess NaOH by sulfuric acid. Lactic was estimated to be 52 wt % while dimer was estimated around 6 wt % of the solution. Water was estimated by gas chromatograph to be 41 wt %. These compositions are consistent with the equilibrium concentrations of monomer and dimer as reported in literature at this concentration level of lactic acid.

Figure 6:
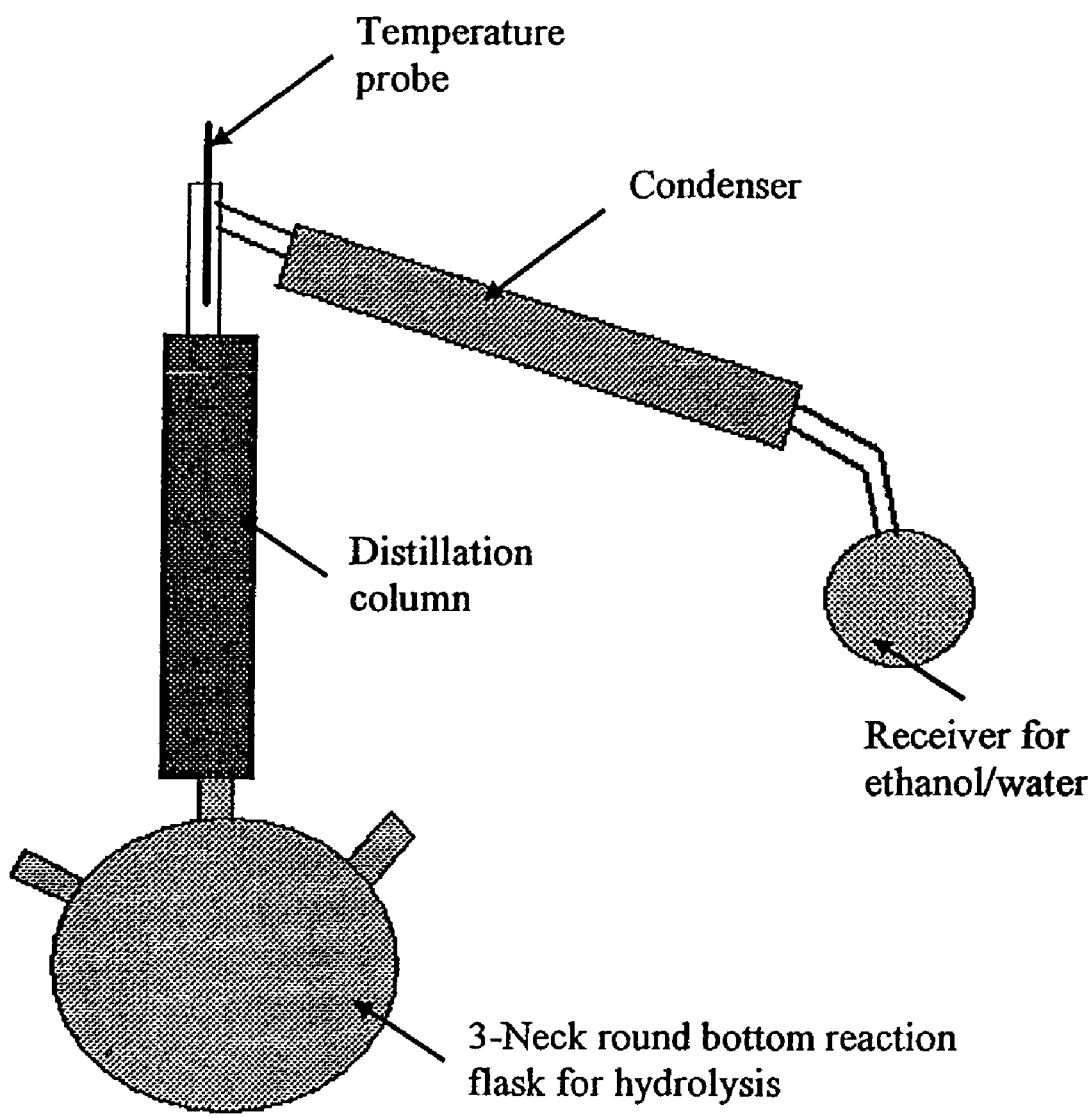
FIG. 6 is a schematic diagram of batch reactive distillation set-up for hydrolysis reaction.
Figure 7:
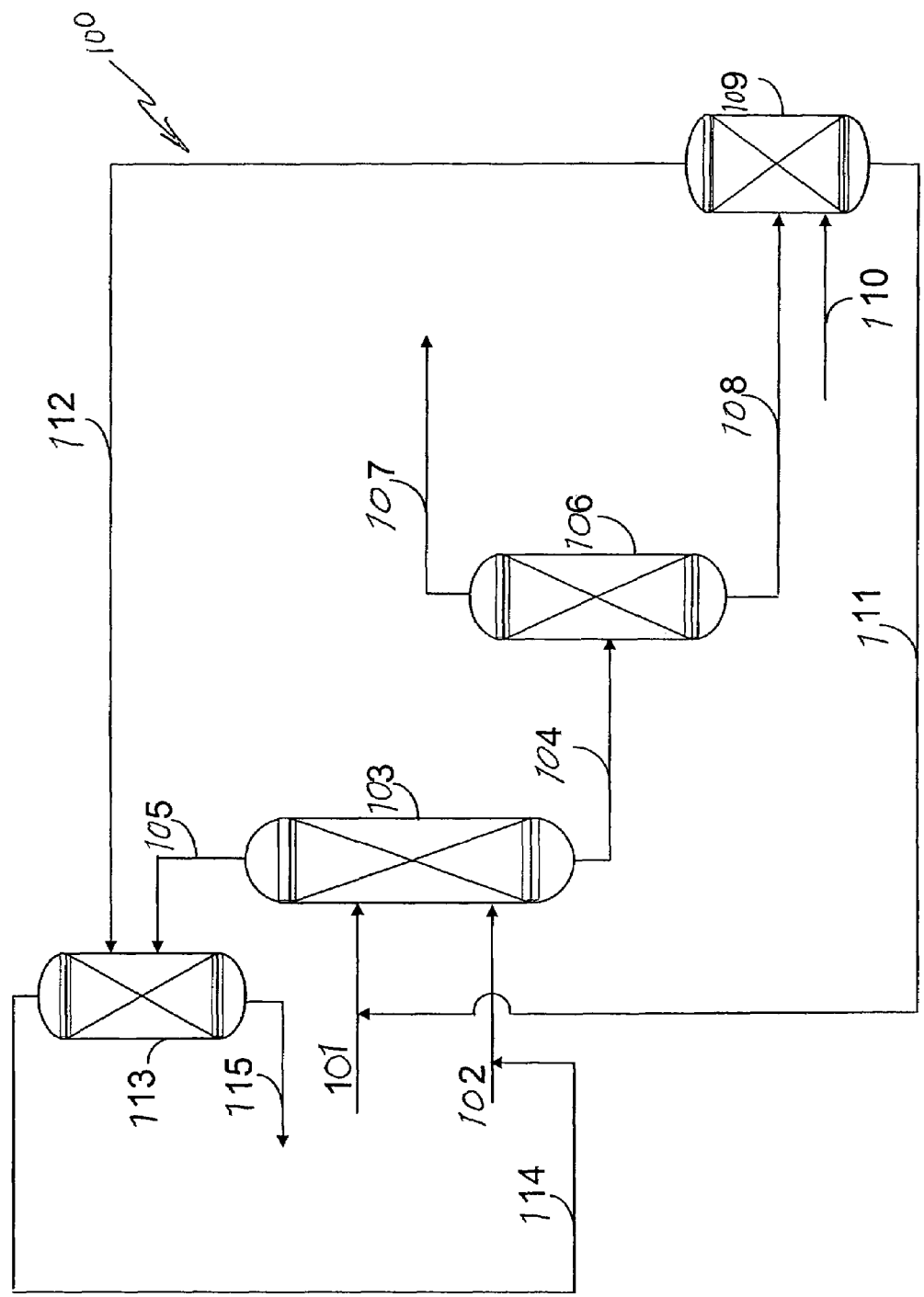
FIG. 7 is a schematic diagram of the process wherein dimers and trimers and other oligomers of a hydroxy acid and their esters, such as lactic acid, are hydrolyzed in column 109 and recycled as lactic acid to column 103 to increase the yield of ethyl lactate.

An efficiency of 95% was obtained in apparatus in FIG. 6. FIG. 7 shows an apparatus 100 wherein dimer ethyl ester and trimer ethyl ester are separated in a separate column 106, hydrolyzed in column 109 and then recycled to lactic acid via recycle line 111 to the lactic acid feed 101 at the upper part of the column 103. The elements of the apparatus are as follows:
101—Lactic acid feed line
102—Ethanol feed line
103—Ethyl lactate synthesis column
104—Bottom stream line from ethyl lactate synthesis
105—Water and unreacted ethanol line
106—Distillation column for separating dimers and trimers
107—Ethyl lactate line
108—Dimer and trimer esters, dimer and trimer acids
109—Hydrolysis column
110—Water
111—Lactic acid recycle line
112—Ethanol/water recycle line
113—Ethanol purification including breaking of EtOH:H$_2$O azeotrope
114—Ethanol recycle
115—Water Using this system of columns, efficiencies of ethyl lactate production of over 95% can be achieved.

It is intended that the foregoing description be only illustrative of the present invention and that the present invention be limited only by the hereinafter appended claims.

We claim:

1. A process for the continuous esterification of a hydroxylated organic acid to produce an organic acid ester in vertical columns by reactive distillation comprising:
   (a) feeding a mixture of a hydroxylated organic acid comprising about 10 to 50% water by weight and comprising the organic acid having between 2 to 8 carbon atoms into an upper port of a first continuous multistage reactive distillation column and an alcohol having 1 to 8 carbon atoms into a lower port of the first reactive distillation column;
   (b) contacting in the first continuous multistage reactive distillation column, the organic acid and the alcohol in countercurrent flow in a reaction zone between the ports at a temperature which reacts the organic acid and the alcohol over an acidic ion exchange resin as a catalyst mounted in structured packing elements and supported as a single unit of the elements in the first reactive distillation column within the reaction zone to form the organic acid ester;
   (c) removing vaporized unreacted alcohol and water from the top of the first reactive distillation column;
   (d) collecting a product stream comprising the organic acid ester, unreacted organic acid, and byproducts selected from the group consisting of organic acid dimers, trimers and oligomers, and organic acid ester dimers, trimers, and oligomers, and combinations thereof from the bottom of the column, wherein the product stream is partially reboiled by a heat exchanger at the bottom of the reactive distillation column so as to heat the organic acid and the alcohol in the reaction zone;

(e) separating the organic acid ester from the unreacted organic acid and the byproducts in a separation column, wherein the organic acid ester is removed through the top of the separation column and the unreacted organic acid and the byproducts are removed through the bottom of the separation column; and (f) reacting the byproducts from the separation column in a second reactive distillation column to at least partially form the organic acid, wherein the organic acid formed in the second reactive distillation column is recycled back to the first reactive distillation column so that the organic acid formed can react with the alcohol to form the organic acid ester when recycled into the first reactive distillation column.

2. The process of claim 1 wherein the unreacted alcohol from the top of the first reactive distillation column is recycled into the lower port of the first reactive distillation column.

3. A process for the continuous esterification of lactic acid to produce a lactic acid ester in vertical columns by reactive distillation comprising:

(a) feeding a mixture of lactic acid comprising about 10 to 50% water by weight into an upper port of a first continuous multistage reactive distillation column and an alcohol having 1 to 8 carbon atoms into a lower port of the first reactive distillation column;

(b) contacting in the first continuous multistage reactive distillation column, the lactic acid and the alcohol in countercurrent flow in a reaction zone between the ports at a temperature which reacts the lactic acid and the alcohol over an acidic ion exchange resin as a catalyst mounted in structured packing elements and supported in the first reactive distillation column within the reaction zone to form the lactic acid ester;

(c) removing vaporized unreacted alcohol and water from the top of the first reactive distillation column;

(d) collecting a product stream comprising the lactic acid ester, unreacted lactic acid, and byproducts selected from the group consisting of lactic acid dimers, trimers and oligomers, and lactic acid ester dimers, trimers, and oligomers, and combinations thereof from the bottom of the first reactive distillation column, wherein the product stream is partially reboiled by a heat exchanger at the bottom of the first reactive distillation column so as to heat the lactic acid and the alcohol in the reaction zone and remove alcohol and water from the lactic acid ester and the byproducts;

(e) separating the lactic acid ester from the unreacted lactic acid and the byproducts in a separation column, wherein the lactic acid ester is removed through the top of the separation column and the unreacted lactic acid and the byproducts are removed through the bottom of the separation column; and (f) reacting the byproducts from the separation column in a second reactive distillation column to at least partially form the lactic acid, wherein the lactic acid formed in the second reactive distillation column is recycled back to the first reactive distillation column so that the lactic acid formed can react to with the alcohol form the lactic acid ester when recycled into the first reactive distillation column.

4. The process of claim 3 wherein the unreacted alcohol from the top of the first reactive distillation column is recycled into the lower port of the first reactive distillation column.

5. The process of claim 3 wherein the feeding of the alcohol relative to the lactic acid is such that a molar ratio of alcohol to lactic acid is maintained between about 1.5 to about 10.0.

6. The process of claim 3 wherein the feeding of the alcohol relative to the feeding of the lactic acid is such that the percentage of lactic acid conversion is greater than 50 percent.

7. A process for the continuous esterification of a hydroxylated organic acid to produce an organic acid ester in vertical columns by reactive distillation comprising:

(a) feeding a mixture of a hydroxylated organic acid comprising about 10 to 50% water by weight and comprising the organic acid having between 2 to 8 carbon atoms into an upper port of a first continuous multistage reactive distillation column and an alcohol having 1 to 8 carbon atoms into a lower port of the first reactive distillation column;

(b) contacting in the first continuous multistage reactive distillation column, the organic acid and the alcohol in countercurrent flow in a reaction zone between the ports at a temperature which reacts the organic acid and the alcohol over an acidic ion exchange resin as a catalyst mounted in structured packing elements and supported as a single unit of the elements in the first reactive distillation column within the reaction zone to form the organic acid ester;

(c) removing vaporized unreacted alcohol and water from the top of the first reactive distillation column;

(d) collecting a product stream comprising the organic acid ester and dimers, trimers and higher oligomers and esters of the dimers, trimers, and higher oligomers of the hydroxylated acid and any unreacted organic acid from the bottom of the column;

(e) separating the organic acid ester from the dimers, trimers and higher oligomers and the esters of the dimers, trimers and higher oligomers of the hydroxylated organic acid and any unreacted organic acid in a separation column;

(f) hydrolyzing, in a second reactive distillation column, the dimers and trimers and higher oligomers and the esters of the dimers, trimers and higher oligomers of the hydroxylated organic acid from the bottom of the separation column to the organic acid by reacting the bottom stream from the separation column with water in the second reactive distillation column; and (g) recycling the organic acid formed in step (f) with the organic acid fed into the first reactive distillation column, and wherein the product stream is reboiled by a heat exchanger at the bottom of the first reactive distillation column so as to heat the organic acid and the alcohol in the reaction zone.

8. The process of claim 7 wherein the unreacted alcohol from the top of the first reactive distillation column is recycled into the lower port of the first reactive distillation column.

9. A process for the continuous esterification of lactic acid to produce a lactic acid ester in vertical columns by reactive distillation comprising:

(a) feeding a mixture of lactic acid comprising about 10 to 50% water by weight into an upper port of a first continuous, multistage reactive distillation column and an alcohol having 1 to 8 carbon atoms into a lower port of the first reactive distillation column;

(b) contacting in the first continuous multistage reactive distillation column the lactic acid and the alcohol in countercurrent flow in a reaction zone between the ports at a temperature which reacts the lactic acid and the alcohol over an acidic ion exchange resin as a catalyst mounted in structured packing elements and supported in the first reactive distillation column within the reaction zone to form the lactic acid ester;

(c) removing vaporized unreacted alcohol and water from the top of the first reactive distillation column;

(d) collecting a product stream comprising the lactic acid ester and dimers, trimers and higher oligomers and esters of the dimers, trimers and higher oligomers of the lactic acid and any unreacted organic acid from the bottom of the column;

(e) separating the lactic acid ester from the dimers, trimers and higher oligomers and their esters and any unreacted organic acid in a separation column (f) hydrolyzing, in a second reactive distillation column, the dimers and trimers and higher oligomers and their esters from the bottom of the separation column to the lactic acid by reacting the bottom stream from the separation column with water in the second reactive distillation column; and (g) recycling the lactic acid formed in step (f) with the lactic acid fed into the first reactive distillation column, and wherein the product stream is reboiled by a heat exchanger at the bottom of the first reactive distillation column so as to heat the lactic acid and the alcohol in the reaction zone.

10. The process of claim 9 wherein the unreacted alcohol from the top of the first reactive distillation column is recycled into the lower port of the first reactive distillation column.

11. The process of claim 9 wherein the feeding of the alcohol relative to the lactic acid is such that a molar ratio of alcohol to lactic acid is maintained between about 1.5 to about 10.0.

12. The process of claim 9 wherein the feeding of the alcohol relative to the feeding of the lactic acid is such that the percentage of lactic acid conversion is greater than 50 percent.

13. A process for the continuous esterification of lactic acid to produce ethyl lactate in vertical columns by reactive distillation comprising:

(a) feeding a mixture of a lactic acid comprising about 10 to 50% water by weight into an upper port of a first continuous multistage reactive distillation column and ethanol into a lower port of the first reactive distillation column;

(b) contacting in the first continuous multistage reactive distillation column, the lactic acid and the ethanol in countercurrent flow in a reaction zone between the ports at a temperature which reacts the lactic acid and the ethanol over an acidic ion exchange resin as a catalyst mounted in structured packing elements and supported as a single unit of the elements in the first reactive distillation column within the reaction zone to form the ethyl lactate;

(c) removing vaporized unreacted ethanol and water from the top of the first reactive distillation column;

(d) collecting a product stream comprising the ethyl lactate, unreacted lactic acid and byproducts selected from the group consisting of lactic acid dimers, trimers and oligomers, and lactic acid ester dimers, trimers, and oligomers, and combinations thereof from the bottom of the first reactive distillation column, wherein the product stream is partially reboiled by a heat exchanger at the bottom of the first reactive distillation column so as to heat the lactic acid and the ethanol in the reaction zone and remove ethanol and water from the ethyl lactate and the byproducts;

(e) separating the ethyl lactate from the unreacted lactic acid and the byproducts in a separation column, wherein the ethyl lactate is removed through the top of the separation column and the unreacted lactic acid and the byproducts are removed through the bottom of the separation column; and (f) reacting the byproducts from the separation column in a second reactive distillation column to at least partially form the lactic acid, wherein the lactic acid formed in the second reactive distillation column is recycled back to the first reactive distillation column so that the lactic acid formed can react with the ethanol to form the ethyl lactate with the ethanol when recycled into the first reactive distillation column.

14. The process of claim 13, wherein the column is operated at atmospheric pressure.

15. The process of claim 13, wherein lactic acid and ethanol are introduced in a molar ratio of ethanol to lactic acid between 3:1 to 9.5:1.

16. The process of claim 13, wherein the ethanol is preheated up to 85° C. before entering the reactive distillation column as a vapor.

17. The process of claim 16, wherein the lactic acid is preheated up to 100° C.

18. The process of claim 13, wherein the treating of the byproducts in the second reactive distillation column comprises hydrolyzing the byproducts with water to form lactic acid and collecting the lactic acid from the bottom of the second reactive distillation column.

19. The process of claim 18, wherein the lactic acid is recycled into the first reactive distillation column at the upper port.

* * * * *